US00PP37171P2

(12) United States Plant Patent
Bourne

(10) Patent No.: US PP37,171 P2
(45) Date of Patent: Dec. 23, 2025

(54) GRAPEVINE NAMED 'SV34-161-275'

(50) Latin Name: ***Vitis vinifera* L.**
Varietal Denomination: SV34-161-275

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 8 days.

(21) Appl. No.: 18/831,548

(22) Filed: Apr. 14, 2025

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./156, 205
See application file for complete search history.

(56) References Cited

U.S. PATENT DOCUMENTS

2016/0044845 P1 * 2/2016 Sheehan ..... Plt./207

* cited by examiner

*Primary Examiner* — Karen M Redden
(74) *Attorney, Agent, or Firm* — Eric C. Cole; Baker Manock & Jensen, PC

(57) ABSTRACT

A new and distinct variety of grapevine plant named 'SV34-161-275' particularly characterized by its medium, red skinned berries that are oblate to ovate in shape with a crisp texture and neutral flavor and which ripen in July in the McFarland, California area.

5 Drawing Sheets

Latin name of the genus and species of the plant claimed: The plant claimed relates to a new and distinct variety of *Vitis vinifera* L.

Variety denomination: The plant claimed shall be known as 'SV34-161-275'.

STATEMENT OF ANY FEDERALLY-SPONSORED RESEARCH AND DEVELOPMENT

The present invention is not subject of Federally-sponsored research or development.

BACKGROUND OF THE INVENTION

The present invention relates to a new and distinct cultivar of grapevine botanically known as *Vitis vinifera* and hereinafter referred to as grapevine named 'SV34-161-275'. As used herein, 'grapevine' refers to all plant parts including, vines, canes, tendrils, leaves, fruit and roots of 'SV34-161-275'. Grapevine named 'SV34-161-275' is the result of an effort to produce an early ripening red table grape. This new cultivar originated from a cross conducted in May 2013 near McFarland, California between female grapevine plant selection 'Red Globe' (unpatented) and male grapevine plant 'Princess' (unpatented). Clusters of fruit resulting from the hybridization were harvested in September and the seeds separated from the fruit were stratified at 2° C. After three months of stratification, seeds were sown in flats in a greenhouse at 26.4° C. Emergent seedlings were grown in the greenhouse at 26.4° C. with 12 hours' illumination under high pressure sodium vapor lamps. The seedling population of 12,809 plants was planted in the field in the spring of 2014 near Delano, California. The new grapevine was selected from this seedling population on Jul. 1, 2015. It was then propagated by cuttings and bench grafted to 'Freedom' (unpatented) rootstock in 2016. The present invention has been found to retain its distinctive characteristics through two successive asexual propagations.

Grapevine named 'SV34-161-275' differs from its female parent grapevine 'Red Globe' (unpatented) in that 'SV34-161-275' has seedless berries whereas 'Red Globe' has seeded berries.

Grapevine named 'SV34-161-275' differs from its male parent grapevine 'Princess' (unpatented) in that 'SV34-161-275' has red berries whereas 'Princess' has white berries.

Grapevine named 'SV34-161-275' most closely resembles commercially available grapevine named 'SV28-100-849' (U.S. Plant Pat. No. 30,541) which also has seedless red berries.

SUMMARY OF THE INVENTION

The following are the most outstanding and distinguishing characteristics of the ripe fruit of this new variety when grown under normal horticultural practices near McFarland, California:

a. Dark red berry color;
b. Crisp texture; and
c. Medium sized berries which more than double in size with gibberellic acid application and trunk girdling.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures.

FIG. 1 Seedling vine with fruit cluster.

FIG. 2 Natural fruit cluster at left and fruit cluster from vine treated with gibberellic acid and trunk girdling at right.

FIG. 3 Leaves and shoots.

FIG. 4 Natural fruit clusters on mature vine.

FIG. 5 Fruit clusters on mature vine treated with gibberellic acid and trunk girdling.

DETAILED BOTANICAL DESCRIPTION

Figure 1:
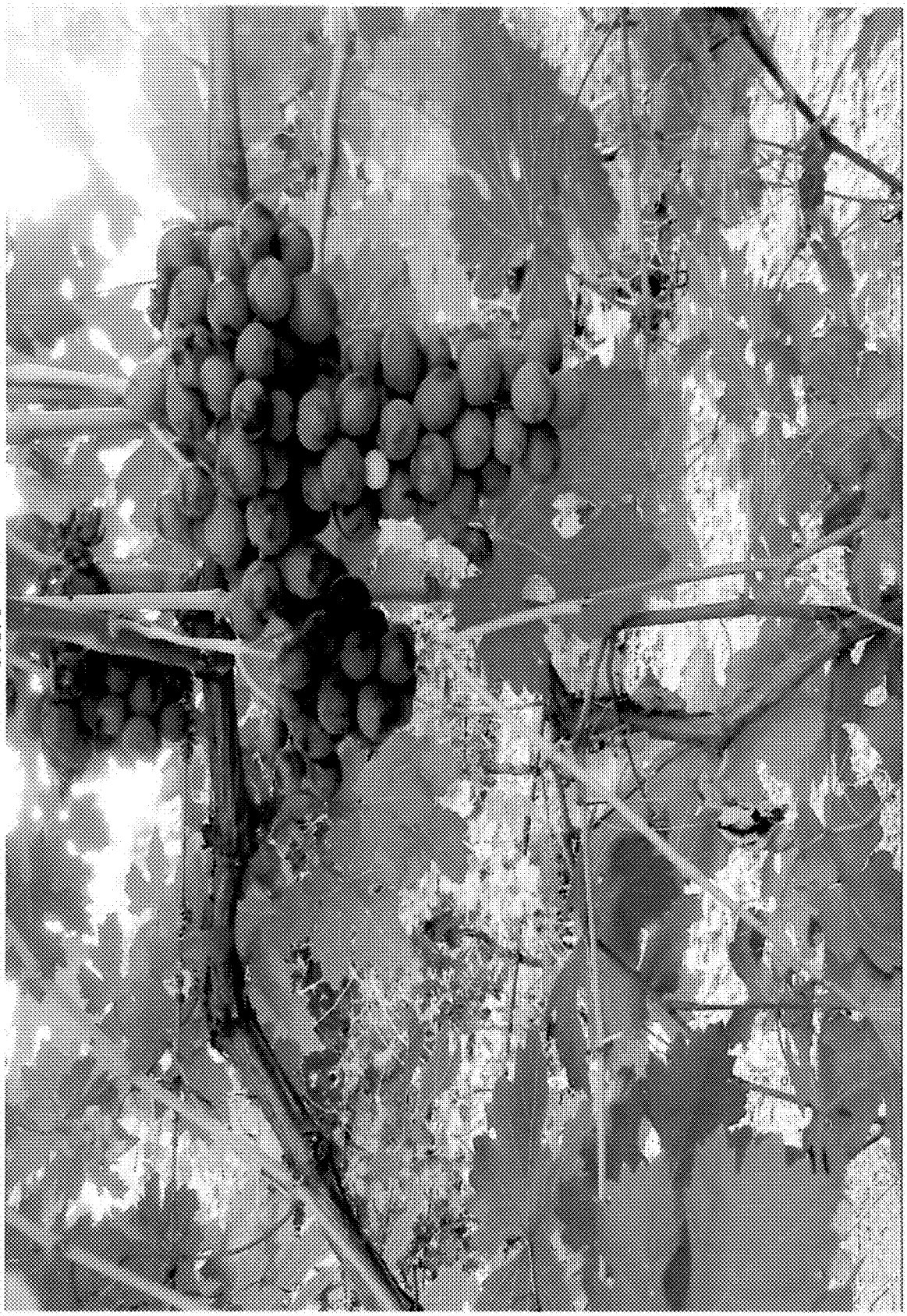
FIG. 1 is a photograph taken in 2015 of the seedling vine.
Figure 2:
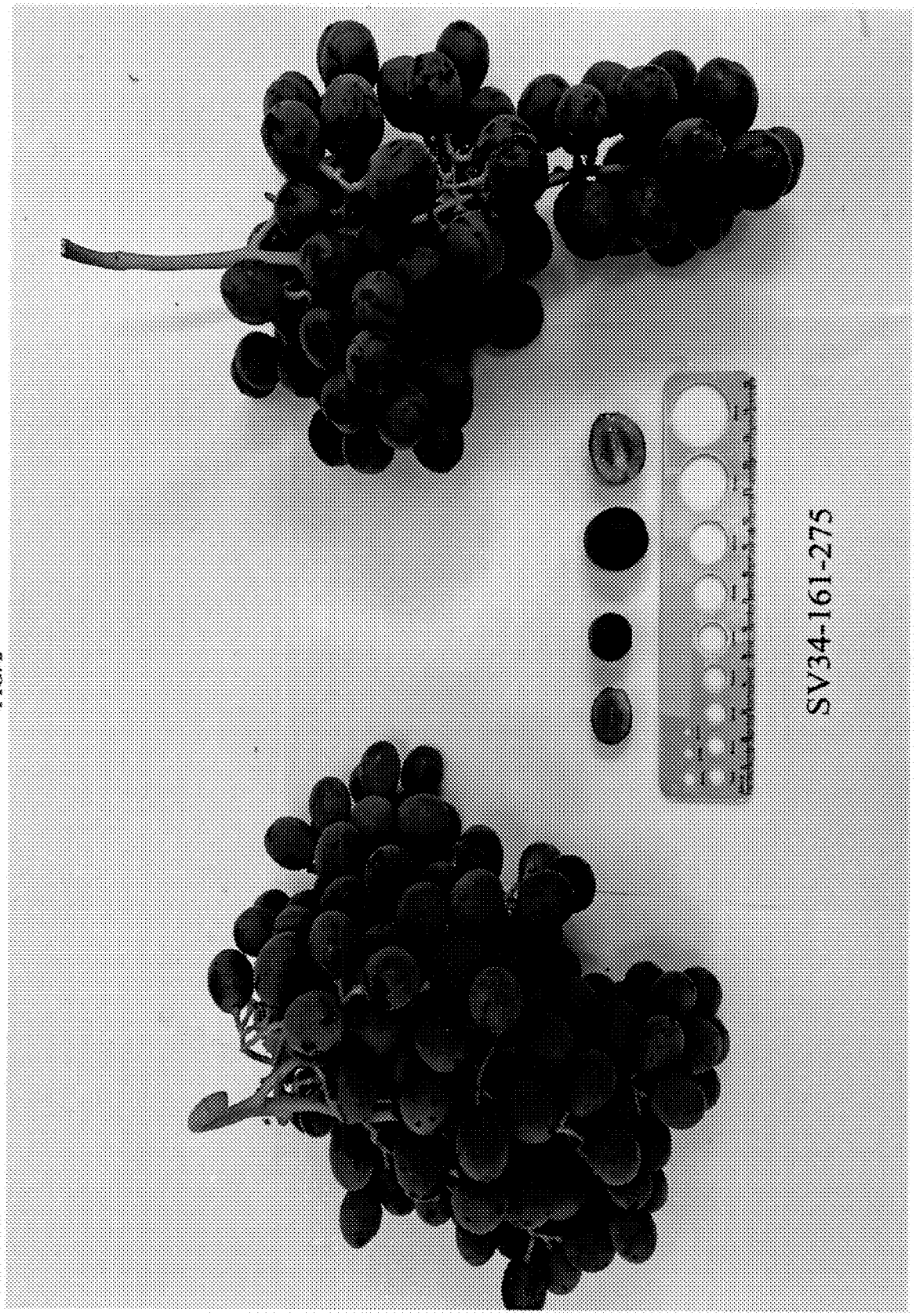
FIG. 2, FIG. 3, FIG. 4, and FIG. 5 are photographs taken in 2024 of leaves and fruit taken from a eight year old plant grown in a field near McFarland, California in 2024.
Figure 3:
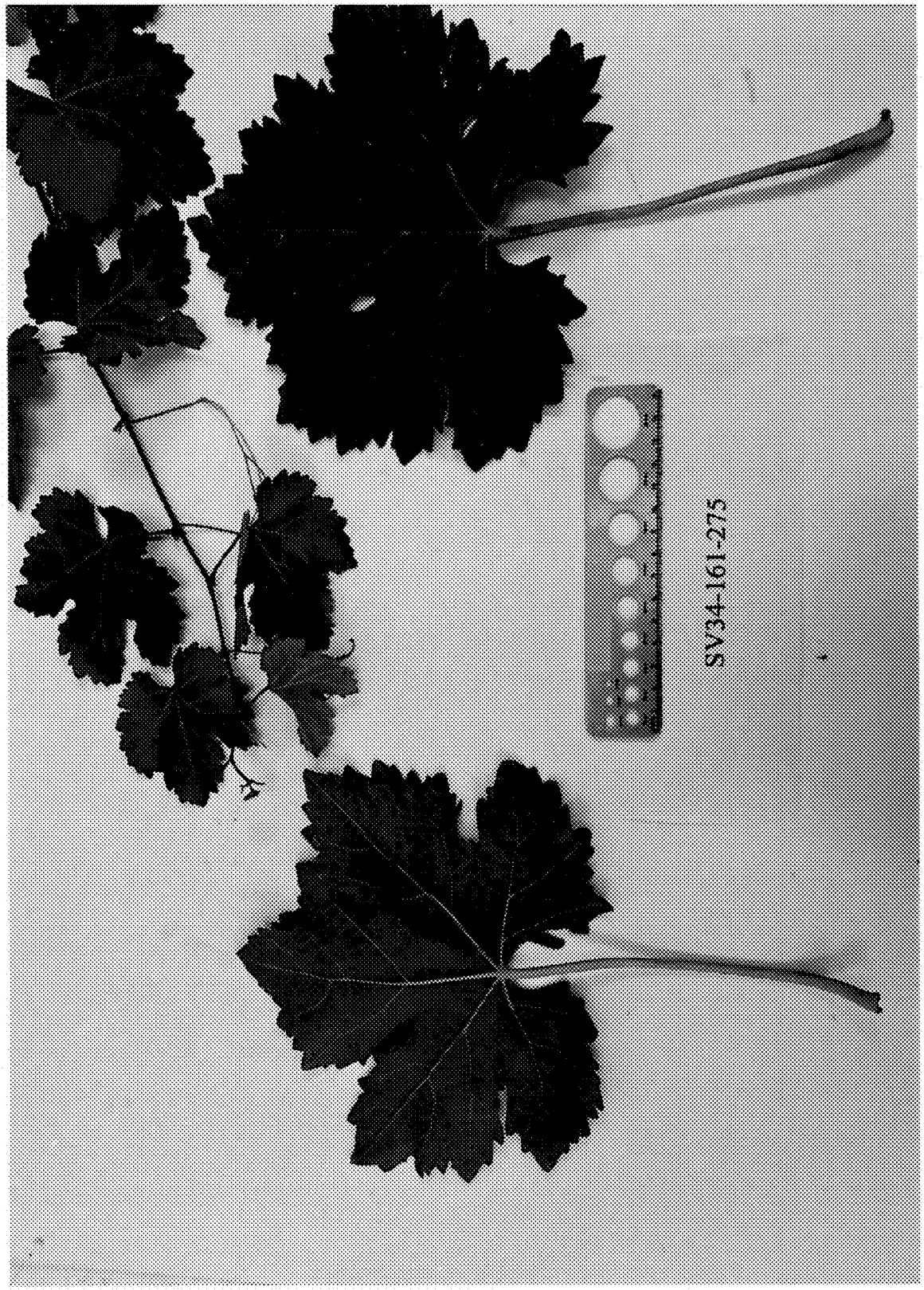
Figure 4:
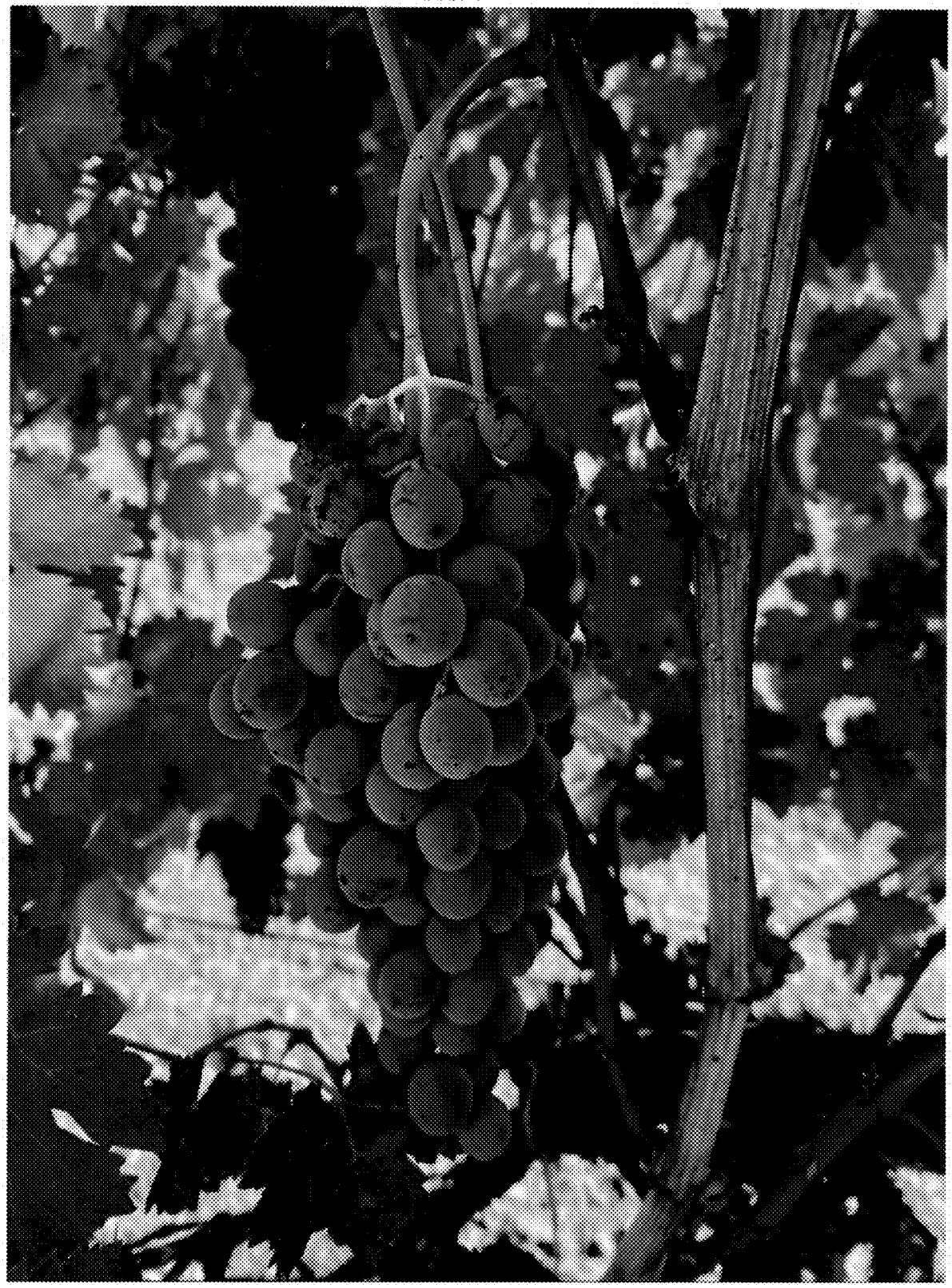
Figure 5:
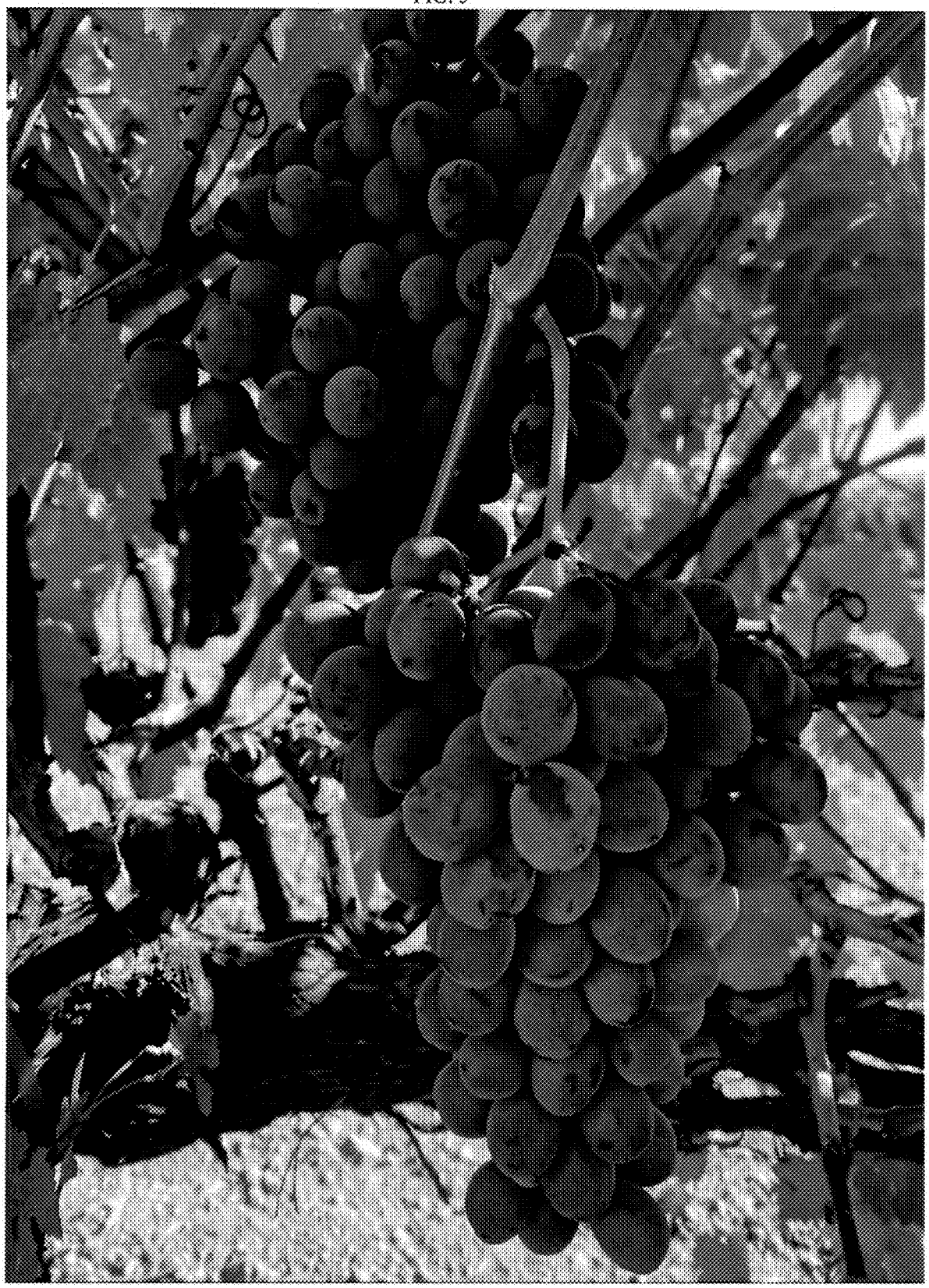

The following detailed description sets forth the distinctive characteristics of 'SV34-161-275'. Descriptions of the new variety apply to vines of 'SV34-161-275' grown on 'Freedom' (unpatented) rootstock at a density of 1,537 vines per hectare grown near McFarland, California in 2024. These vines were in their sixth year of production, having been planted in 2016. These descriptions are believed to apply generally to the new variety grown under similar circumstances elsewhere. References to color correspond to the Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV34-161-275'.

Plant:

*Vigor*.—vines spur-pruned and shoot thinned to 32 shoots average 150.94 cm of growth per cane.

*Density of foliage*.—Moderate.

*Productivity*.—Moderate, up to 29,000 kg/hectare.

*Hardiness*.—Hardiness observed to 0° C.

*Rootstock*.—'Freedom' (unpatented).

Trunk:

*Shape*.—Broadly elliptical.

*Straps*.—Long, split.

*Surface texture*.—Shaggy.

*Trunk circumference*.—10.28 in (26.10 cm).

*Inner bark color*.—RHS Greyed-Orange group 165A.

*Outer bark color*.—RHS Brown group N200A.

Mature leaves:

*Average blade length*.—15.94 cm.

*Average blade width*.—19.82 cm.

*Size of blade*.—Large.

*Shape*.—Pentagonal.

*Number of lobes*.—5.

*Anthocyanin coloration of main veins on the upper side of the blade*.—Present, very weak and only at central junction.

*Mature leaf profile*.—Undulate, slightly cupped upward around entire margin.

*Blistering* (*upper surface*).—Absent.

*Leaf blade tip*.—Slightly cupped downward.

*Margins*.—Lobed, serrated, undulating.

*Apex*.—Broadly acuminate.

*Bases*.—Sagittate.

*Thickness*.—Medium.

*Undulation of blade between main and lateral veins*.—Slight.

*Shape of teeth*.—Mixture of both sides straight and both sides convex.

*Length of tip*.—11.8 mm.

*Width of tip*.—17.4 mm.

*Ratio length/width of tip*.—About 7:10.

*General shape of petiole sinus*.—Wide open to half open.

*Tooth at petiole sinus*.—Absent.

*Petiole sinus limited by veins*.—Absent.

*Shape of upper lateral sinus*.—Lobes strongly overlapping.

*Depth of upper lateral sinus*.—Medium (avg. 2.74 cm).

*Prostrate hairs between veins* (*lower surface*).—Absent.

*Erect hairs between veins* (*lower surface*).—Absent.

*Prostrate hairs on main veins* (*lower surface*).—Only erect hairs at junctions.

*Density of erect hairs on main veins* (*lower surface*).—Sparse along main veins, medium at junctions.

*Prostrate hairs on main veins* (*upper surface*).—Sparse to none.

*Upper surface: Summer color: RHS Green group* 139A. Surface texture: Dull. Surface appearance: Smooth. Goffering of blade: Absent.

*Lower surface*.—Summer color: RHS Green group 138A. Anthocyanin coloration of main veins on lower leaf surface: Absent. Anthocyanin coloration on laterals: Absent. Glossiness: None to low. Pubescence distal portion of surface: Absent. Surface texture: Rough. Surface appearance: Dull.

*Petiole*.—Length: 15.66 cm. Length of petiole compared to middle vein: About equal. Density of prostrate hairs: Absent. Density of erect hairs: Absent. Shape of base of petiole sinus: Half open. Color: In shade: RHS Yellow-Green group 144C. In sun: RHS Red-Purple group 60C.

Tendrils:

*Number and Pattern*.—Trifurcated; forming irregularly at all nodes above 5.

*Length*.—20.86 cm.

*Diameter*.—5 mm.

*Texture*.—Smooth.

*Color*.—RHS Yellow-Green group 144C.

Growing tips (Young shoots):

*Prostrate hair on tips*.—Sparse.

*Erect hairs on tip*.—Absent.

*Anthocyanin coloration of prostrate hairs on tips*.—Absent.

*Color*.—RHS Yellow-Green group N144C.

*Anthocyanins*.—Absent.

*Shape*.—Rounded.

*Apex*.—Fully open.

Green summer shoots:

*Shoot attitude*.—Erect.

*Internode color dorsal surface*.—RHS Red-Purple group 61A.

*Internode color ventral surface*.—RHS Yellow-Green group 145C.

*Node color dorsal surface*.—RHS Red-Purple group 64A.

*Node color ventral surface*.—RHS Yellow-Green group 145C.

*Density of erect hairs on internodes*.—Absent.

Woody shoot:

*Canes*.—Internode length: 10.05 cm. Internode diameter: 1.2 cm. Width at node: 18.6 mm. Surface: Smooth. Main color: RHS Greyed-Orange group 164A.

*Buds*.—Shape: conical Length: 7.3 mm. Width: 5.5 mm. Height: 6.1 mm. Color: RHS Brown group 200B.

Flowers:

*Flower sex*.—Hermaphrodite.

*Position of first flowering nodes*.—4th and 5th node.

*Number of inflorescences per shoot*.—1.

*Flower cluster width*.—10.2 cm.

*Flower cluster length*.—19.3 cm.

*Cluster stem color*.—RHS Yellow-Green group 144B.

*Calyptra color*.—RHS Yellow-Green group 144A.

*Ovary length*.—2 mm.

*Ovary width*.—1 mm.

*Ovary color*.—RHS Green group 143B.

*Filament length*.—2 mm.

*Filament color*.—RHS Yellow-Green group 145B.

*Anther length*.—1 mm.

*Anther color*.—RHS Yellow group 10B.

*Date of full bloom*.—May 14, 2024.

Fruit:

*Ripening period*.—Early mid-season at McFarland, California.

*Date of ripening*.—Jul. 22, 2022 at McFarland, California.

*Use*.—Fresh market.

*Keeping quality*.—Very good.

*Shipping quality*.—Good.

*Date of first harvest*.—

*Solids-sugar*.—High, about 20 brix at full maturity.

*Refractometer test*.—19 brix.

*Bunch*.—Size: Large (with gibberellic acid treatment and girdling). Length (peduncle excluded): Natural, without gibberellic acid treatment: 20 cm. With gibberellic acid treatment and girdling: 19.8 cm. Width: Natural, without gibberellic acid treatment: 14.5 cm. With gibberellic acid treatment and girdling: 16.7 cm. Weight: Natural, without gibberellic acid treatment: 341 g. With gibberellic acid treatment (grams): 745 g. Density: Natural, without gibberellic acid treatment: Well-filled. With gibberellic acid treatment and girdling: Somewhat tight. Number of berries: Natural, without gibberellic acid treatment: 152. With gibberellic acid treatment and girdling: 150. Form: Conical.

*Peduncle*.—Length: Natural, without gibberellic acid treatment: 3.4 cm. With gibberellic acid treatment and girdling: 5.9 cm. Lignification: Very sparse to none. Color: RHS Yellow-Green group 144B.

*Berry*.—Size: Medium. Uniformity of size: Uniform. Weight Natural, without gibberellic acid treatment: 2.4 g. With gibberellic acid treatment: 5.8 g. Shape: Natural, without gibberellic acid treatment: Round. With gibberellic acid treatment: Oblate with some ovate. Presence of seeds: one or two small, soft rudimentary seeds less than 1.0 mm in length. Cross section: Circular. Dimensions: Longitudinal axis: Natural, without gibberellic acid treatment: 1.96 cm. With gibberellic acid treatment and girdling: 2.4 cm. Horizontal axis:

Natural, without gibberellic acid treatment: 1.8 cm. With gibberellic acid treatment and girdling: 2.38 cm. Circumference: Natural, without gibberellic acid treatment: 1.56 cm. With gibberellic acid treatment and girdling: 2.16 cm. Skin color (without bloom): RHS Greyed-Purple group N186B. Coloration of flesh: Translucent, RHS Yellow-Green group 144D. Juiciness of flesh: Very juicy. Berry firmness: Very firm. Particular flavor: Neutral, typical vinifera (decent sugar, low acid). Bloom (cuticular wax): Medium-strong. Pedicel length (cm): Natural, without gibberellic acid treatment: 0.98 cm. With gibberellic acid treatment and girdling: 0.94 cm. Berry separation from pedicel: With difficultly.

*Skin*.—Thickness: Medium. Texture: Crisp. Reticulation: Absent. Roughness: Absent. Tenacity: Skin tenacious to flesh. Tendency to crack: None observed.

Disease and Insect Resistance: No particular resistance or susceptibility has been observed. Normal disease control practices can be used.

Having thus described and illustrated our new variety of grapevine, I claim:

1. A new and distinct variety of grapevine plant named 'SV34-161-275', substantially as illustrated and described herein.

* * * * *